United States Patent [19]
Hakky et al.

[11] Patent Number: 5,234,000
[45] Date of Patent: Aug. 10, 1993

[54] AUTOMATIC BIOPSY DEVICE HOUSING A PLURALITY OF STYLETS

[76] Inventors: Said I. Hakky, 8547 Merrimoor Boulevard East, Largo, Fla. 34647-3145; Perry B. Hudson, 2225 Park St. North, St. Petersburg, Fla. 33710

[21] Appl. No.: 951,611

[22] Filed: Sep. 25, 1992

[51] Int. Cl.$^5$ .............................................. A61B 10/00
[52] U.S. Cl. ...................................... 128/754; 128/751; 606/171
[58] Field of Search ............... 128/749, 751, 752, 753, 128/754, 755, 760, 763, 762, 770; 606/167, 168, 170, 171, 183, 186, 185, 188; 206/363, 364, 365, 366, 370, 375, 380, 443

[56] References Cited

U.S. PATENT DOCUMENTS

| | | | |
|---|---|---|---|
| 3,949,747 | 4/1976 | Hevesy | 128/754 |
| 4,476,864 | 10/1984 | Tezel | 128/755 |
| 4,766,907 | 8/1988 | de Groot et al. | 128/754 |
| 4,907,599 | 3/1990 | Taylor | 128/754 |
| 4,946,035 | 8/1990 | Grimm et al. | 206/366 |
| 5,012,818 | 5/1991 | Joishy | 128/754 |
| 5,133,359 | 7/1992 | Kedem | 128/754 |
| 5,143,084 | 9/1992 | Macemon et al. | 128/771 |
| 5,156,160 | 10/1992 | Bennett | 128/754 |

FOREIGN PATENT DOCUMENTS

269164 6/1988 European Pat. Off. ............ 606/186

OTHER PUBLICATIONS

Quinton Instruments "Operator Manual: Model 7 mm Hydraulic Biopsy Instrument" pp. 1–15, Seattle, Washington, Jun. 1976.

Primary Examiner—Max Hindenburg
Assistant Examiner—Guy V. Tucker
Attorney, Agent, or Firm—Caesar, Rivise, Bernstein, Cohen & Pokotilow, Ltd.

[57] ABSTRACT

An automatic biopsy device for taking plural samples of tissue of a patient. The device is pneumatically operated in response to the depressing of a trigger by the operator and makes use of a removable cassette in which a plurality of stylets are located. The stylets are disposed on a moveable tray within the cassette and are arranged to be selectively positioned within the device for propulsion through a releasably mounted cannula at a high speed into the tissue to be sampled. Each stylet includes a groove adjacent its distal end into which the tissue to be sampled enters when the cannula is propelled into the tissue. Thereafter and in automatic response to the propulsion of the stylet through the cannula into the tissue, the cannula is propelled over the stylet to excise the tissue within the stylet's recess. The propulsion of the stylets and cannula is so rapid that the tissue sampling procedure is virtually pain-free. The stylet and cannula are retracted in response to release of the trigger so that the stylet is withdrawn into the cassette. The cassette is removable from the device and can be taken to a laboratory for analysis of the tissue samples, all the while protecting the tissue samples and the personnel handling them.

36 Claims, 6 Drawing Sheets

AUTOMATIC BIOPSY DEVICE HOUSING A PLURALITY OF STYLETS

FIELD OF THE INVENTION

The present invention relates to biopsy devices and more particularly to a powered automatic biopsy device which is capable of taking a plurality of biopsies in rapid sequence.

In the study of tissue, a biopsy, which is a sample of tissue extracted from the body, is taken. One common biopsy device used today includes a needle or stylet into which an indentation or recess has been cut. The stylet is manually inserted into the tissue to be sampled and a hollow tube or cannula, with a very sharp cutting edge, is then slid over the stylet so that a sample of tissue is excised and entrapped within the recess when the cutting edge of the cannula extends past the recess.

Another manual device also includes the cannula and stylet, which are manually pushed into the body to penetrate the organ whose tissue is to be sampled. The surgeon, then using two hands, must retract the cannula so that the indentation in the stylet is exposed. The cannula is pushed forward again so that its cutting edge can excise a plug of tissue. The cannula and stylet are then removed from the body. The excised tissue is placed in a fluid solution to protect it and keep it from drying out so that the tissue may later be tested.

Mechanically operated biopsy device are disclosed in the patent literature. For example, in U.S. Pat. No. 4,917,100 (Nottke) there is disclosed a spring operated device including a needle or stylet having a groove therein and which is located within a cannula.

Another spring loaded biopsy device is disclosed in U.S. Pat. No. 4,976,269 (Mehl). This device uses a gun shaped handle with a trigger which automatically projects the cannula forward to excise the plug of tissue. First the gun is cocked and then the stylet and cannula are inserted into the body so that they penetrate the organ of which a tissue sample is desired. When the trigger is pulled the cannula withdraws a sufficient distance to expose the recess in the stylet. The spring mechanism then forces the cannula forward so that its cutting edge can excise a plug of tissue which is held in the recess in the stylet. This device can be operated by a single hand of the surgeon. Also, the stylet with the tissue sample can be removed while the cannula remains in place inside the organ for other samples.

The aforementioned manual and spring loaded devices have several important shortcomings. In particular, the manual devices must be manipulated by the surgeon using two hands which are often wet and slippery during the operation. The spring loaded gun devices are difficult to operate during surgery, not only because the hands of the surgeon may be wet and slippery, but also because considerable force is required to compress the powerful springs used in the device.

Many surgical procedures now require a plurality of biopsy samples to be taken. For example, up to six or more samples of tissue are required when testing the tissues of the prostrate gland and other body organs. In order to take multiple tissue samples using the prior art manual biopsy devices, each time a sample is taken, the device must be removed, and a new puncturing of the organ made. This action is tedious and time consuming. Moreover, multiple manual penetrations of the organ are typically somewhat painful. Moreover, such penetrations are subject to bleeding and infection.

Although the device of the Mehl patent allows the cannula to remain in the organ between samples, the stylet itself must be manually removed from the biopsy device so that the test sample can be removed, which is again tedious and time consuming. The stylet is then manually inserted back into the biopsy device and through the cannula into the organ.

Another and significant drawback of the prior art is that the stylets bearing the tissue samples must be manually handled. This exposes those persons handling the stylets to danger of infection, e.g., HIV infection.

Finally, with present devices, the stylets and samples are handled on an individual basis. The tissue samples are often damaged or destroyed due to improper handling. There is also possibility of loss or mislabelling of the samples.

A need thus exists for an powered biopsy device which can take a plurality of tissue samples painlessly in rapid sequence, and wherein stylets bearing the tissue samples taken are automatically placed into a case which can be removed from the device for study in such a way that the handling personnel and the samples are protected.

OBJECTS OF THE INVENTION

Accordingly, it is the general object of this invention to provide a biopsy device which overcomes the shortcomings of the prior art.

It is a further object of this invention to provide an automatic biopsy device which applies power to the stylet and cannula for rapid insertion and removal from the tissue being sampled.

It is still a further object of this invention to provide an automatic biopsy device which is capable of taking a plurality of tissue samples in rapid succession.

It is yet a further object of this invention to provide an automatic biopsy device which controls the penetration of the stylet and cannula into the organ being sampled.

It is yet a further object of the instant invention to provide an automatic biopsy device which does not require manual penetration of the organ whose tissue is being sampled.

It is yet a further object of this invention to provide an automatic biopsy device which does not require the manual handling of each individual stylet after the sample has been taken.

It is yet a further object of this invention to provide an automatic biopsy device which provides for protected and safe handling of the stylets and biopsy samples after the samples have been taken thereby.

SUMMARY OF THE INVENTION

These and other objects of this invention are achieved by providing a device for taking a plurality of samples of tissue from a living being. The device comprises a housing having a portion arranged to be held by a person using the device, a cannula having a proximal portion and a distal portion and being coupled to the housing. A plurality of stylets are located in the housing, with each of the stylets having a proximal end, a distal end, and a recess located adjacent the distal end.

An actuating system, e.g., a pair of pneumatic cylinders, associated valves, and an operating trigger, are provided for selectively propelling each of the stylets through the cannula and into the body of the being, e.g., in response to the depression of the trigger, so that a portion of the tissue enters into the recess of the selected stylet. The actuating system propels, e.g., in automatic response, the cannula over the selected stylet to cause the distal portion of the cannula to excise the portion of tissue within the recess of the selected stylet.

The actuating system is also arranged, e.g., upon release of the trigger, to move the selected stylet and the cannula out of tissue in the body of the being.

In accordance with one preferred aspect of this invention the stylets are propelled into the tissue being sampled at a high rate of speed and the cannula is propelled over the stylets at a high rate of speed. These actions tend to minimize, if not eliminate, pain to the patient.

In accordance with another preferred aspect of the invention the stylets are located within a cassette which is releasably secured to the device. The stylets with the tissue samples therein are retracted by the device into the cassette for removal as a unit therefrom for testing so that the samples and personnel handling them are protected.

DESCRIPTION OF THE DRAWING

Other objects and many of the attendant advantages of this invention will be readily appreciated when the same becomes better understood by reference to the following detailed description, when considered in connection with the accompanying drawing, wherein.

DETAILED DESCRIPTION OF THE PREFERRED EMBODIMENT

Figure 1:
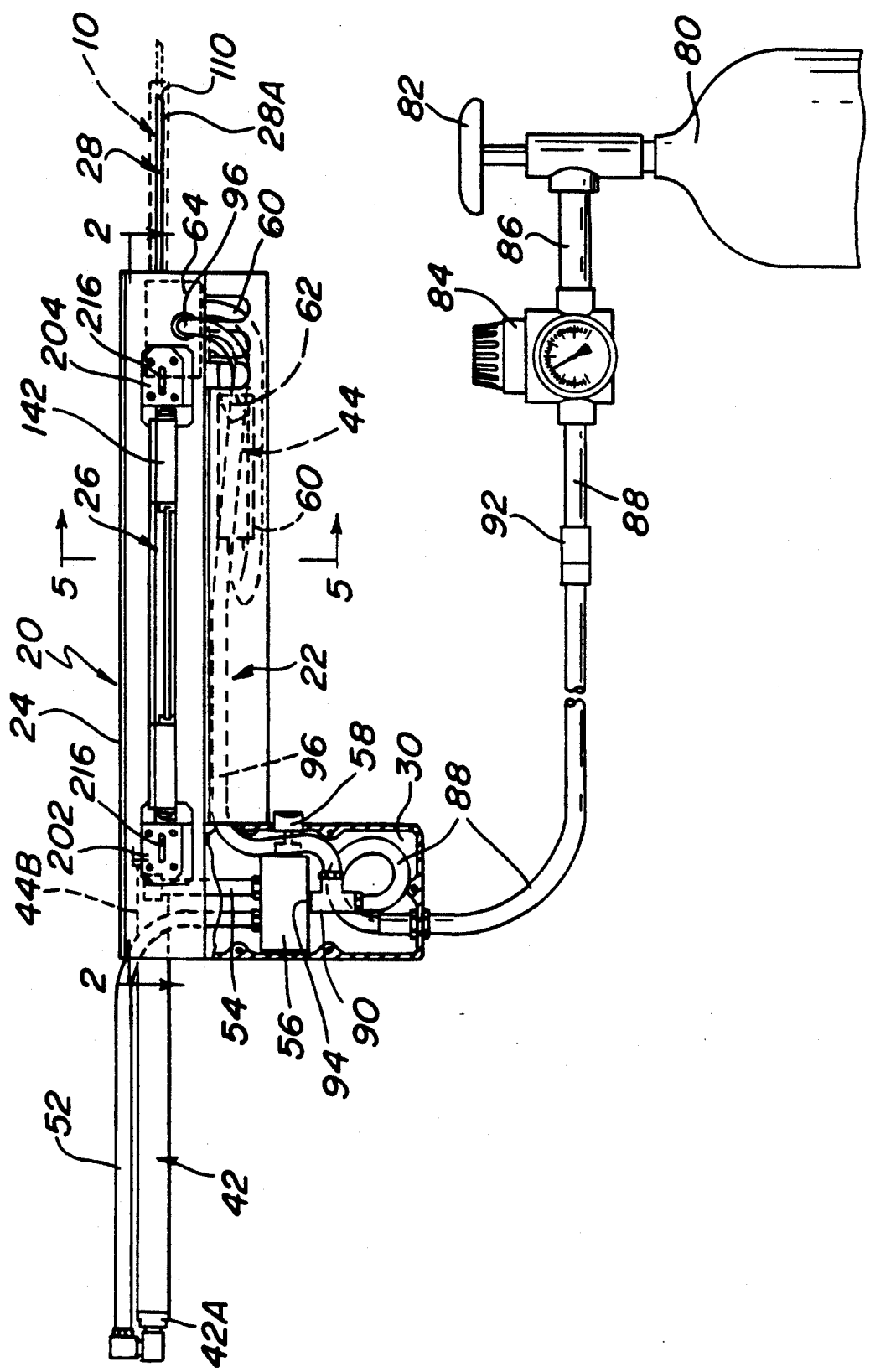
FIG. 1 is a side elevational view, partially in section, of the automatic biopsy device of the present invention.

Referring now to the various figures of the drawing where in like reference characters refer to like parts, there is shown an automatic biopsy instrument or device 20 constructed in accordance with the instant invention. The device 20 is arranged to be held in the hand of a surgeon or other medical person to take plural tissue samples from a patient for study. The device 20 basically comprises a gun-shaped housing 22, formed of any suitable material, e.g., aluminum, having a body portion 24 for releasable mounting therein a cassette 26. At the distal end of the housing is a cannula assembly 28. This assembly basically comprises an elongated tube having a distal end in the form of a cutting edge. The proximal end of the cannula assembly comprises a block which serves to releasably mount the cannula assembly on the device 20.

The device is arranged so that it can be readily manipulated by the surgeon so that the cannula 28A is inserted within the body of the patient, either percutaneously, or through a body lumen or orifice, e.g., transrectally, transuretherally, etc., to the site of the internal tissue to be sampled. To that end, the device's housing 22 includes a handle 30 located below the body portion 24 so that it can be readily held in the surgeon's hand to orient the device, as desired, and to operate it.

The cassette 26 will be described in detail later. Suffice it for now to state that the cassette is a generally U-shaped structure having a hollow interior into which a tray 32 is located. The tray 32 is arranged to hold a plurality of needle-like members or "stylets" 34A-34F. Each stylet includes a pointed distal end having an elongated notch or recess adjacent thereto. The recess is arranged to receive a portion of tissue to be excised so that when the cannula is slid thereover (as will be described later) the tissue within the recess is cut or sliced away from the remaining tissue of the patient's body and is held within the recess.

In particular, and as will also be described in detail later, the tray bearing the stylets is arranged to be moved to a position within the housing so that a stylet is aligned with the cannula 28A. Thereafter the device is operated to cause that stylet to be extended, e.g., propelled, almost instantaneously out of the free end of the cannula 28A into the tissue to be sampled to enable a portion of that tissue to enter the notch in the stylet's distal end. Thereafter, and automatically, the cannula is extended, e.g., propelled, almost instantaneously over the extended stylet so that the portion of the tissue within the stylet's recess is excised, i.e., sheared off by the passing cannula. The device is then operated to retract both the stylet and the cannula from the tissue being sampled, with the stylet with the tissue sample therein being retracted into the cassette.

In accordance with the preferred embodiment of this invention, device 20 may be used to sequentially take tissue samples by the use of respective stylets, and to withdraw those stylets into the cassette, until all of the desired samples are taken. At that time the cassette may be removed from the device 20 and transported to a laboratory for analysis of the tissue samples. A new cassette having a tray of fresh stylets may then be inserted into the device and a new cannula mounted on the device to replace the used cannula. Since only the cannula and the stylets contact the patient, and since these components are replaced, the device 20 is now ready for reuse on another patient.

The extension and retraction of the stylets 34A-34F and the cannula 28 are accomplished in the disclosed embodiment by a pneumatic drive system 40. That system is merely exemplary and is shown in the schematic diagram of FIG. 7. As can be seen therein the system 40 basically comprises first and second pneumatic cylinders 42 and 44 respectively. The cylinders are driven by a compressed gas, e.g., carbon dioxide. The first cylinder 42 includes a piston 46 which is coupled to a catch 50 (to be described later) for selectively engaging the proximal end of each stylet 24A-24F to effect the extension and retraction of the engaged stylet. The second cylinder 44 includes piston 48 which is coupled to a carrier 52 (to be described later). The carrier 52 supports the cannula assembly 28 and particularly its mounting block thereon to effect the extension and retraction of the cannula with respect to the housing.

As will be described later, the tray 32 is arranged to be sequentially moved with respect to the housing when the cassette is mounted within the housing to bring selected ones of the stylets into alignment with the cannula 28 so that they can be extended therethrough by the operation of the cylinder 42, and then the cannula is automatically extended over the extended stylet by the operation of the cylinder 44.

The movement of the piston 46 of the cylinder 42 in the distal direction to cause the extension of a selected stylet out of the cassette and through the cannula 28A to penetrate or pierce the tissue to be sampled is effected by providing the compressed gas into the proximal end 42A of the pneumatic cylinder housing 42 via an input line 52. The movement of the piston in the proximal direction to cause the retraction of the stylet back through the cannula 28 and into the cassette 26 is effected by providing the compressed gas into the distal end 42B of the pneumatic cylinder 42 via another input line 54.

In order to control which of the input lines 52 or 54 provides the compressed gas to the cylinder 42, a reversing valve 56 and associated components (to be described later) are provided within the housing. The operation of the reversing valve 56 is controlled by a manually actuatable trigger or button 58 located on the device's handle 30. The trigger is coupled to the valve 56 and is arranged so that when it is depressed the valve 56 switches from the state shown in FIG. 7 to the state allowing the compressed gas (from a source to be described later) to enter into input line 52. This action immediately causes the piston 46 and the stylet coupled thereto to move in the distal direction to extend the distal end of the stylet and its associated recess out of the free end of the cannula and into the tissue of the patient.

The movement of the piston 48 of the cylinder 44 in the proximal direction to extend the cannula over now extended stylet to excise the portion of the tissue within the stylet's groove is effected by providing compressed gas into the proximal end 44A of the second pneumatic cylinder 44 via an input line 60. This extension of the cannula over the extended stylet occurs automatically virtually immediately after the stylet has been extended into the tissue to be sampled (as will be described later).

The movement of the piston 48 in the proximal direction to cause the retraction of the cannula out of the tissue of the patient is effected by providing the compressed gas into the distal end 44B of the cylinder via another input line 62.

In order to control which of the input lines 60 or 62 provides the compressed gas to the cylinder 44, a second reversing valve 64, is provided. The valve 64 is mounted at the distal end of the device 20 and includes a plunger 66 which is arranged to be engaged by a pivotal lever arm 68.

The lever arm is mounted at the distal end of the housing adjacent the cannula-supporting carrier 52 and is arranged to be engaged by the catch 50 on the piston rod 46A when the piston rod of cylinder 42 is propelled outward, i.e. once the stylet has been extended into the tissue to be excised. This action causes the pivotally arm 68 to swing into engagement with the plunger 66, thereby depressing the plunger and causing the reversing valve 64 connected thereto to assume the state wherein the compressed gas is provided via line 60 into the proximal end 44A of the cylinder 44. Accordingly, the piston 48 is automatically immediately propelled in the proximal direction, thereby carrying the carriage 52 with the cannula assembly 28 mounted thereon outward over the extended stylet to excise the tissue within the stylet's groove.

When the trigger 58 is released, the compressed gas is permitted to flow through the reversing valve 56 into the line 54, whereupon the piston 46 of the cylinder 42 is propelled in the proximal direction, thereby retracting the stylet back into the housing. When the catch 50 on the piston reaches the location of the lever arm 68 it releases that arm, whereupon the plunger 66 is freed and the second reversing valve 64 immediately changes state so that the compressed carbon dioxide is provided via line 62 into the proximal end of the second cylinder 44. This action propels the piston 48 of that cylinder in the proximal direction, thereby retracting the carrier and the cannula mounted thereon. When the pistons of both cylinders are fully retracted, that is they are in the position shown in FIG. 2 and 7, the cannula will have been withdrawn from the tissue site. Moreover, the stylet which has the tissue sample in its groove will now be completely retracted within a groove (to be described later) in the tray 32 within the cassette 26. The device 20 is now ready to take another tissue sample via the extension of the next stylet and followed by the extension of the cannula assembly 28 over that stylet.

The compressed gas for the system 40 is provided from any suitable source, e.g., a compressed $CO_2$ cylinder 80, via an adjustable valve 82. The outlet of the valve 82 is connected to a metering device 84 via a line or conduit 86. The output of the metering device 84 is provided via line or conduit 88 to the input of a T-coupling 90. A filter 92 (FIG. 1) is preferably included in the conduit 88. The T-coupling includes a pair of output lines 94 and 96, which are connected to the inputs of the reversing valves 56 and 64, respectively.

Figure 7:
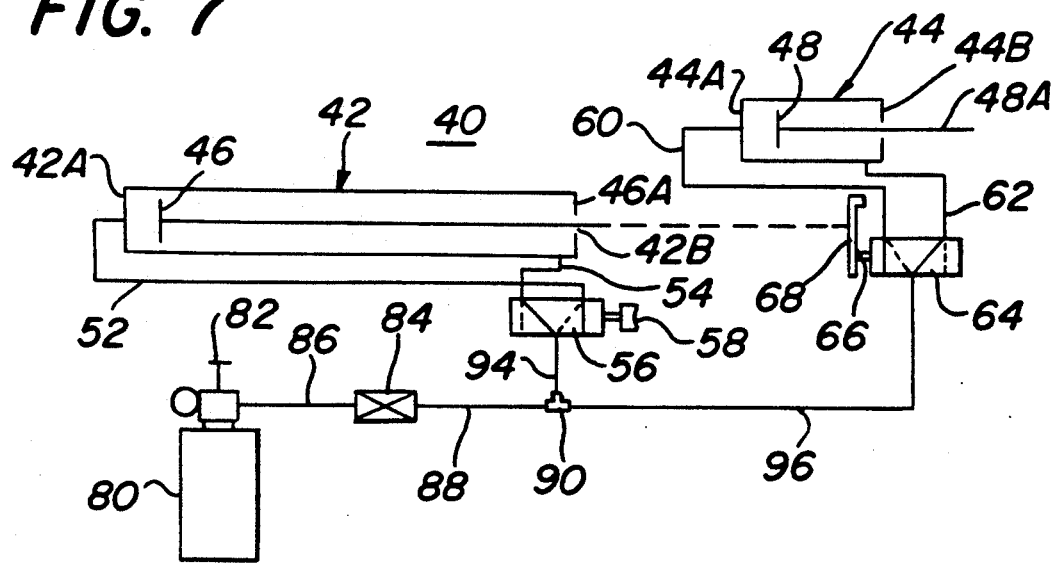
FIG. 7 is a schematic diagram of the pneumatic system which powers the device of FIG. 1.

In FIG. 7 the solid diagonal lines in the reversing valves 56 and 64 represent the quiescent state of those valves, i.e., the state of the device when it is ready to take a tissue sample, prior to the depressing of the trigger 58. In such a state the pistons 46 and 48 are located to the rear (proximally) in the pneumatic cylinders 42 and 44, respectively. The dotted diagonal lines in the reversing valves represent the connections made when the trigger is depressed and the plunger 66 is pushed forward by the lever arm 68. Each of the reversing valves includes at least one gas release path which are designated by the solid vertical lines in those valves to allow the existing gas in the pneumatic cylinders 42 and 44 to be released therefrom so as not to oppose the movement of the pistons 46 and 48, respectively, either in the forward (distal) or the backward (proximal) direction. This is of considerable importance to ensure that the pistons move virtually instantaneously.

Figure 3:
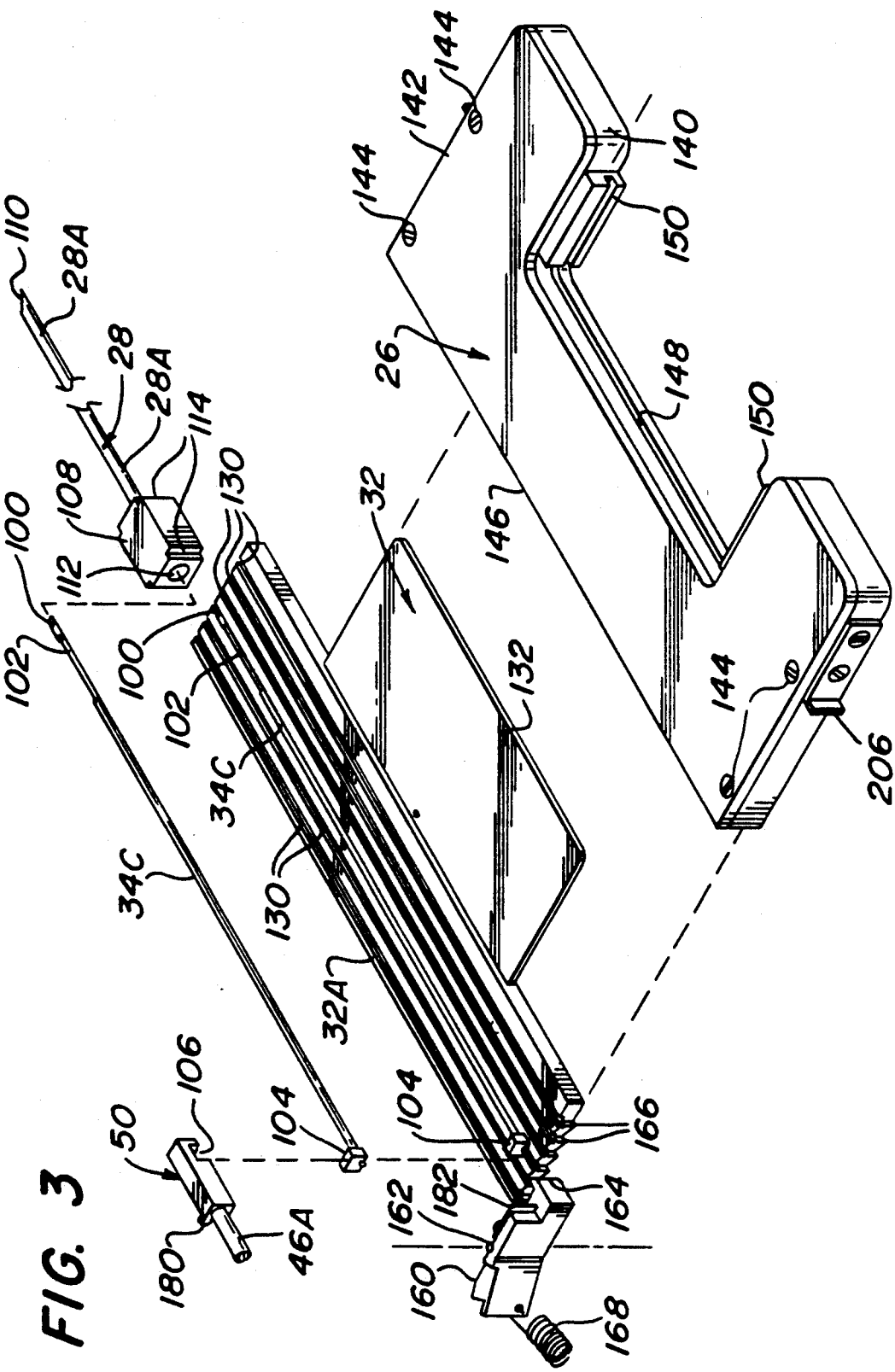
FIG. 3 is an enlarged exploded isometric view of the stylet cassette, the stylet, and the cannula of the device of FIG. 1.

The details of the stylets 34A–34C and the cannula 28 will now be described with reference to FIG. 3. As can be seen therein each stylet is an elongated needle or rod-like member having a distal end which is sharpened, i.e., cut at an angle, to provide a piercing point 100. An elongated recess or groove 102 is provided in the stylet adjacent its piercing tip 100. The groove 102 serves as the repository for the tissue to be excised. The proximal end of the stylet includes a block of 104. The block 104 is arranged to be selectively received within a groove 106 in the catch 50. When the block is within that groove the movement of the piston rod 46A either proximally or distally causes the concomitant movement of the stylet therewith.

The stylet and cannula can be formed of any suitable material. In accordance with the preferred embodiment invention the each is formed of stainless steel.

The cannula assembly 28 basically comprises an elongated tubular member having a free distal end 110 cut at an angle to the longitudinal axis of the cannula to form a sharp cutting edge. The proximal end of the cannula assembly 28 is in the form of the heretofore mentioned mounting block 108. The block 108 is formed of any suitable material, e.g., plastic, and includes a flared inlet toward 112 at its proximal face and which communicates with the hollow interior of the tubular cannula 28A. Each corner of the block 108 includes a recess 114 therein which is arranged to receive respective edges of upstanding walls 52A of the cannula carrier 52 (see FIG. 4) to hold the cannula in place on the carrier. A set screw 116 is provided in one of the walls 52A of the carrier 52 to engage the block 108 to lock the cannula assembly 28 on the carrier 52.

The carrier 52 is mounted on a pair of rod-like guide rails 118 to enable the carrier to be slid along the rails, i.e., reciprocated, by the movement of the piston of cylinder 44. The guide rails 118 are mounted within the housing via a bracket 120 and associated screws 122. The cannula 28A extends out of the housing of via a slot 124 in the front end thereof when the cannula assembly is mounted on the carrier 52.

As mentioned earlier, the cassette 26 includes a tray 32 therein. As can be seen clearly in FIG. 3, the tray 32 includes plural grooves 130 disposed in a side-by-side array along the length of the tray i.e., from its distal end to its proximal end. Each groove 130 is arranged to receive a respective one of the stylets 34A-34F therein. The tray includes a large planar tab or projection 132 extending outward from one side thereof. The projection 132 is arranged to be received within respective portions of the cassette to facilitate the positioning of the tray with respect to the cassette (as will be described later). As will also be described later the tray is arranged to be moved to sequentially align its grooves 130 with the cannula assembly 28 so that the stylet in each of the grooves can be selectively brought into alignment with the passageway through cannula 28A for passage therethrough into the tissue to be sampled.

The cassette 26 basically comprises a generally U-shaped member having a lower body portion or base 140 formed of any suitable material, e.g., aluminum, and a cover, e.g., clear plexiglass, 142 releasably secured thereover via plural threaded fasteners 144. The cassette includes an open side 146, i.e., the base 140 doesn't include an upstanding sidewall on that side so that the cover 142 is spaced over the base. This open side serves as the entrance for inserting a tray full of stylets into the cassette. In particular, tray 32 is arranged to be inserted within the cassette 26 through the open end 146 of the cassette so that the tab 132 of the tray extends through a slot 148 in the sidewall of the base 140 and into a pair of guide slots 150. The guide slots are provided on opposite sides of the slot 148 to receive the projection 132 of the tray 32 when the tray is located within the cassette 26. When the tray is fully within the cassette the cove 142 of the cassette completely overlays every groove 130 of the tray.

The tray 32 is arranged to be moved laterally out of the cassette, that is through the open end 146, by pressing on the edge of the tab 132 once the cassette is in place within the device's housing. This aligns the groove 130 holding the stylet 34F, i.e., the first stylet to be ejected, with the catch 50 on the piston rod 46A and with the entrance port 112 on the cannula assembly 28. The device is now ready to take a tissue sample using stylet 34F as described earlier. Once that has been accomplished the device moves the tray into the cassette until that the next groove, i.e., the groove holding stylet 34E, is in axial alignment with the cannula 28 so that stylet 34E can be extended thereout to take a second tissue sample. Each operation of the device to take a sample results in the movement of the tray to a new position to bring the next stylet into alignment with the cannula for propulsion therethrough to take the next tissue sample.

Figure 2:
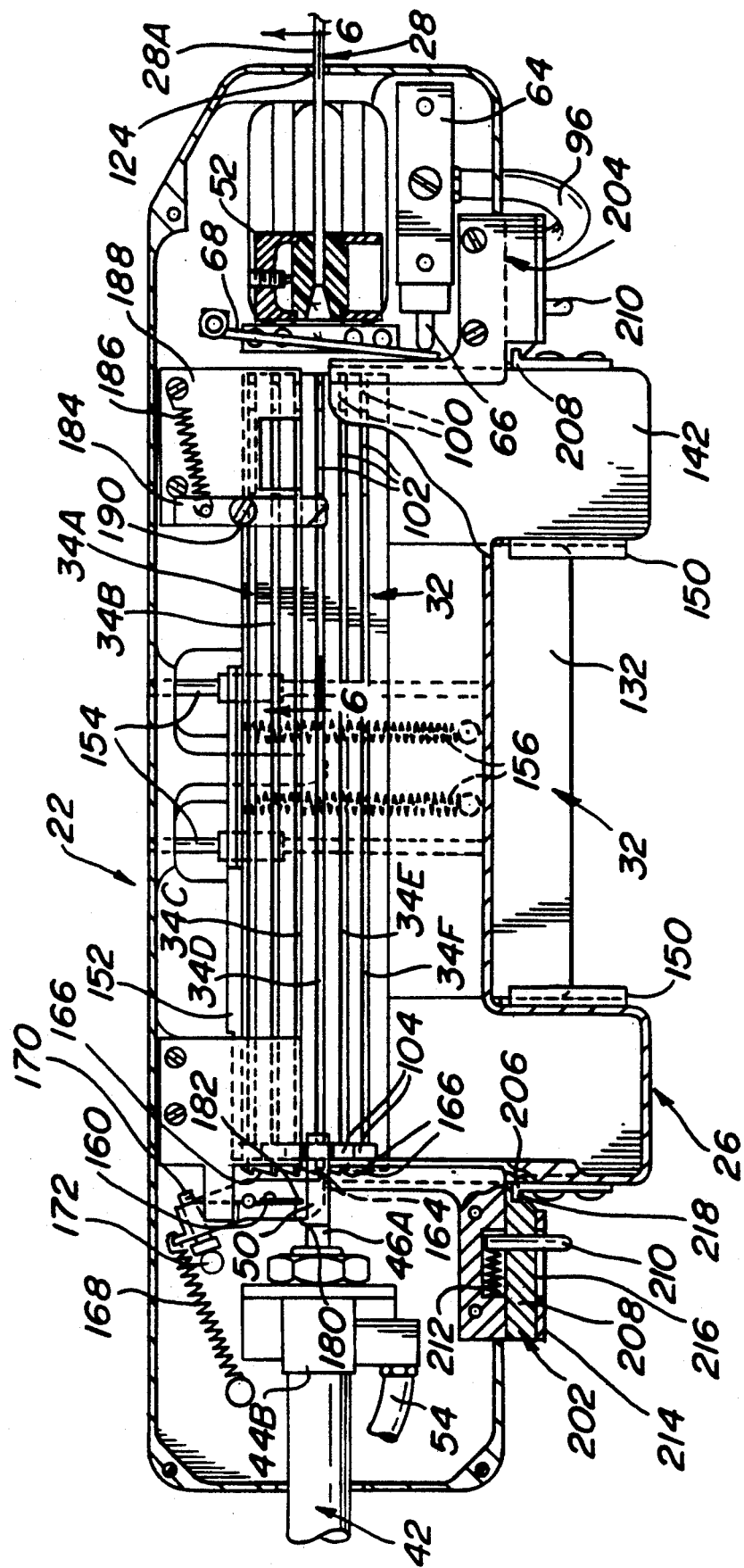
FIG. 2 is an enlarged sectional view of the device taken along the line 2—2 of FIG. 1.
Figure 5:
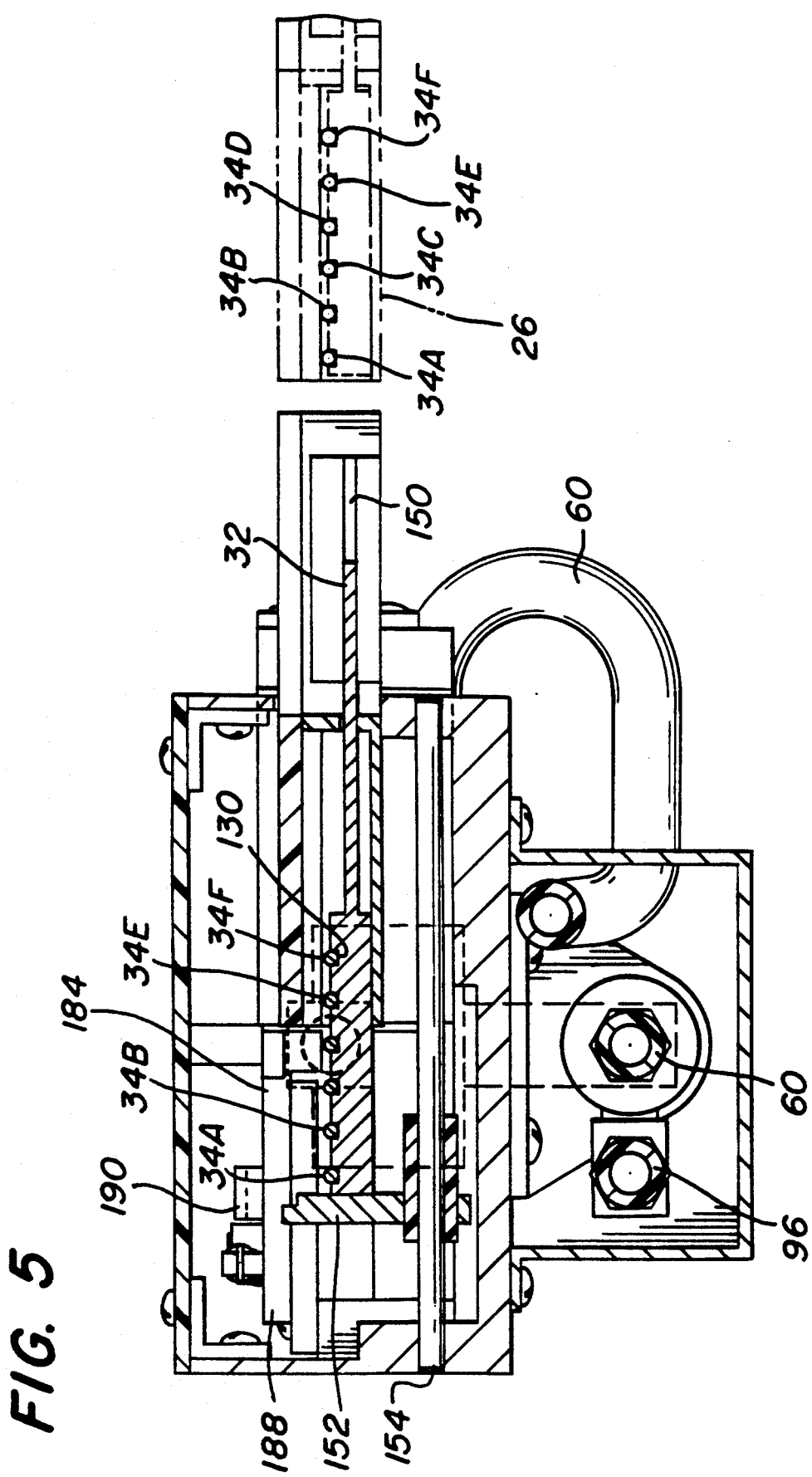
FIG. 5 is as an enlarged sectional view of the device taken along the line 5—5 of FIG. 1 and showing in phantom lines a stylet cassette which has been removed from the device.
Figure 6:
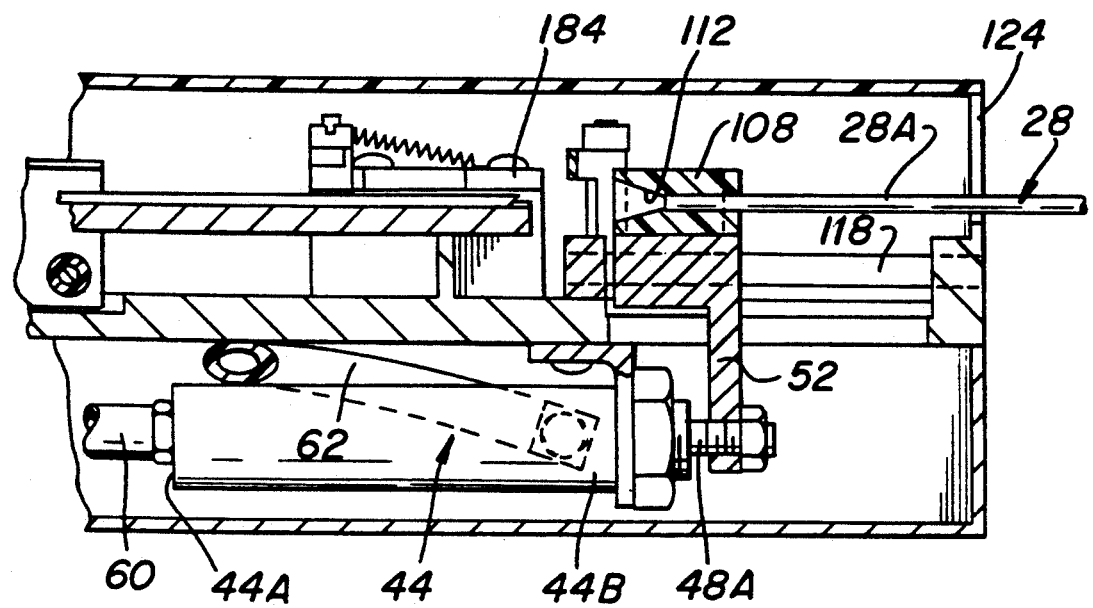
FIG. 6 is a sectional view of the distal end of the device taken along the line 6—6 of FIG. 2.

The means for moving the tray 32 to sequentially align the stylets with the cannula 28 basically comprises a spring based pusher plate 152 (FIGS. 2 and 5). The plate 152 is arranged to engage the edge 32A of the tray disposed opposite to the projection 132. The pusher plate 152 is mounted on a pair of transversely extending rods 154 mounted in the housing. A pair of tension springs 156 are mounted within the housing secured to the plate 152 to bias the plate into an engagement with the edge 32A of the tray to sequentially carry the tray deeper into the cassette 26 after each tissue sampling operation. To that end, a ratchet mechanism is provided to hold the tray against the bias of the springs 156 so that the next successive grooves 130 having a stylet therein will be aligned with the cannula 28 after the previously stylet has taken a tissue sample.

The ratchet mechanism basically comprises a lever arm 160 mounted on a pivot rod 162 in the housing. The lever 160 includes a pawl-like projection or hook 164 arranged to sequentially engage respective detentes or grooves 166 in the proximal edge of the tray 32. Each groove has a respective detent or groove associated therewith. A biasing spring 168 is connected to the lever 160 and to the housing to tend to pull the pawl-like hook 164 into the detente or groove 66 aligned therewith. This action prevents the tray from moving with respect to the cassette notwithstanding the bias force provided by the pusher plate 152. A set screw 170 is provided in the lever arm 160 adjacent its connection to the spring 168. The set screw is arranged to abut an upstanding post 172 in the housing to enable the precise adjustment of the lever arm 160 to ensure that it operates properly with respect to the tray.

When a tray with each of its grooves having a stylet is located within the cassette and cassette is inserted into the device 20 and the projection 132 pressed to extend the tray partially outside of the cassette's open side, as described earlier, the pawl-like hook 164 of the lever arm 160 engages the detente or groove 166 of the tray closest to the projection 132. This action aligns the stylet 34F the passageway through cannula 28A. At this time, the block 104 at the proximal end of the stylet 34F will be located within the groove 106 in the catch 50 at the distal end of the piston rod 46A. Thus, the operation of the cylinder 42, as described heretofore, will propel the stylet 34F down its groove 130 so that the stylet's piercing tip 100 enters the flared entrance port 112 in the cannula. The continued motion of the piston in the distal direction causes the stylet to pass through the cannula's passageway and out its sharp end 110 to pierce the tissue to be sampled. Once the stylet has moved to the position wherein it is extended as far as it needs to be so that the tissue to be sampled will be in the stylet's groove, the cylinder 44 is automatically operated to immediately slide the cannula over the extended stylet to excise that tissue sample. These sequential extension actions occur at high speed (virtually instantaneously), so that the patient does not experience any pain or trauma. In this regard in accordance with a preferred aspect of this invention, the cylinders 42 and 44 are arranged to propel the stylet and cannula at speeds greater than the speed at which the body transmits pain impulses, e.g., at speeds in excess of 5-6 meters per second.

After the tissue within the stylet has been excised and the device's trigger released both the stylet and the cannula are retracted, as described heretofore. When the stylet 34F is retracted back into the housing it re-enters the groove 130 in the tray from which it was ejected. As can be seen clearly in FIGS. 3 and 4. The catch 50 includes a spur 180 thereon. This spur 180 is arranged to momentarily engage a leaf spring 182 mounted on the pivot lever 160 to momentarily pivot the lever 160 in the clockwise direction as view in FIG. 2, whereupon the pawl-like hook 164 moves out of the first of the detentes or grooves 166, whereupon the bias provided by the plate 152 slides the tray 32 one groove into the cassette, i.e., until the pawl-like extension 164 enters into the second detente or recess 166, whereupon the stylet 34E will be aligned with the cannula. At this time the block 104 of the stylet 34A will be within the groove 106 of the catch 50, so that when the operator depresses the trigger 58 the stylet 34E will be propelled out of the device in the same manner as described heretofore to take a second tissue sample.

Figure 4:
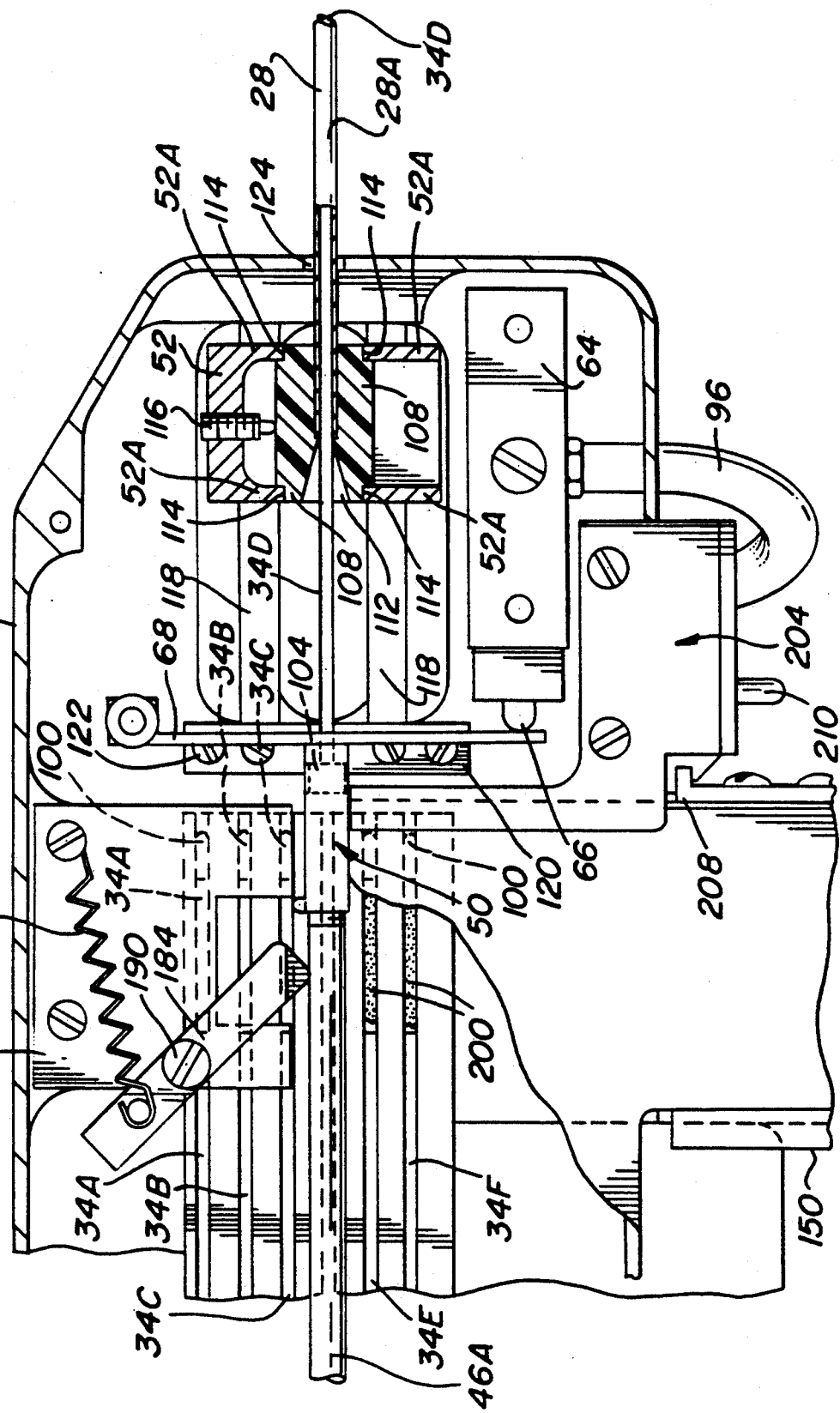
FIG. 4 is an enlarged top plan view, partially in section, of the distal end of the device of FIG. 1.

As can be seen in FIG. 4, a pivotable, spring biased bar 184 is mounted within the housing to overlay the groove 130 in the tray that is then aligned with the cannula's passageway to prevent the stylet located in that groove from jumping out of the groove when the stylet is propelled forward. The pivoting bar 184 is biased by a tension spring 186 and is mounted on a bracket 188 located over the proximal end of the tray 32. The bar 184 is pivotable about a screw 190 so that it can be pivoted out of the way of the catch 50 passing thereby when the device is in the state shown in FIG. 4, i.e., when the stylet is extended fully out of the cannula so that the catch 50 engages the pivot arm 68. The biasing spring 186 returns the lever arm 184 to the position overlying the groove when the catch 50 has been retracted to the proximal position shown in FIG. 2.

As will be appreciated by those skilled in the art each time that the trigger 58 is released to enable the retraction of the stylet back into its associated groove in the tray, the spur 180 on the catch 50 will monetarily engages the spring 182 to thereby release the pawl-like hook 164 from the associated groove or detente 166 and thereby enable the pusher bar to move the tray one groove further into the cassette to align the next stylet with the cannula.

The cassette 26 is arranged to be releasably secured within the device's housing by means of a pair of latch assemblies 202 and 204. These assemblies are best seen in FIG. 2. Each latch assembly is of identical construction. The latch assembly 202 is mounted on one side of the device's housing 24 immediately adjacent the handle 30, while the latch assembly 204 is mounted on the housing portion of 24 adjacent the cannula assembly 28. The latch assembly 202 is arranged to releasable engage a flanged tab 206 screwed onto one end of the sidewall of the cassette body, while the latch assembly 204 is adapted to engage a similarly constructed tab 208 screwed on the sidewall at the other end of the cassette body. Each latch assembly basically comprises a sliding catch 208, an actuating pin 210, a biasing spring 212, and a cover plate 214 having a slot 216 therein. The catch 208 of assembly 202 includes a groove 218 adapted to receive the flanged portion of the tab 206 therein to hold the cassette in place. While the catch 208 of assembly 204 includes a similar groove to receive the flanged portion of tab 208. Thus, as should be appreciated by those skilled in the art when the cassette is inserted into the housing the flanged portion of tabs 206 and 208 ride along the tapered surface of the catches 208 of assemblies 202 and 204, respectively, thereby pushing those catches to the left and right, respectively, as shown in FIG. 2 until the flanges of the tabs 206 enter their recesses 218. At this time the biasing springs will hold the catches in place. In order to remove the cassette from the housing, all that is required is to push the pin 210 to the left as shown in FIG. 2 against the bias of spring 212, thereby releasing the flange of tab 206 from the groove 218. The latch assembly 204 is released from the flange of tab 208 in a similar manner so that the cassette can be grasped by the user and pulled out of the device's housing.

The overall operation of the automatic biopsy device 20 to take plural tissue samples will now be discussed. To that end, a cassette having fresh stylets therein is inserted into the housing by operating the latches 202 and 204. The stylet bearing tray is then pushed partially out of the cassette by pressing on its projection 132 against the bias of the biasing plate so that the pawl-like hook 164 mates with the detent of the groove 130 in which the first stylet to be ejected, i.e., stylet 34F, is located.

The surgeon then manipulates the device 20 by its handle 30 so that the free end of the cannula 28A inserted in the patient's body is located at a position adjacent the tissue to be sampled. It should be pointed out at this juncture that when the device 20 is to be introduced through a lumen or other opening in the patient's body, e.g., transurethrally, transrectally, a tubular shield 10, (shown by the phantom lines in FIG. 1) is placed over the cannula 28A to protect the patient from its sharp end 110.

The aiming of the tip of the cannula to the desired position and orientation is preferably effected by use of ultrasound or any other form of imaging.

Some present medical procedures call for multiple, e.g., six, biopsy samples of a patient. The device 20 of this invention enables the surgeon to take such samples without having to withdraw the device from the patient's body or to reload it with stylets. In this regard, with the device disclosed herein the surgeon can quickly and easily take up to six tissue samples by merely aiming instrument and pressing its trigger for each sample to be taken. Moreover, the stylets are quite long, e.g., 170 mm, and are arranged to extend out of the cannula by a substantial distance, so that the tip 110 of the cannula need not be manually inserted in the organ to be tested, as has characterized the prior art. Thus, in a number of cases and depending upon the length of the stylet used, there may be no need to manually puncture the organ or tissue from which the sample is to be taken, i.e., the tip of the cannula need not be manual pushed by the surgeon into the organ or tissue. Instead, the pneumatic cylinder will provide such action at high speed thereby reducing pain or trauma.

For the taking of biopsies through the surface of the body, e.g., to biopsy organs such as the liver or kidney, the local area of the body surface is first anesthetized and the skin and underlying tissue is pierced by manually pressing the cannula 28 so that its piercing tip 110 enters into the patient's body to a location adjacent the tissue/organ to be sampled. The device may then be operated as described earlier, i.e., depressing the trigger 58 in sequence to cause the stylets 34A to 34F to take tissue samples in sequence. This operation can accomplished virtually as fast as the trigger can be depressed, released, redepressed, re-released, and so on.

After all the biopsies have been taken, the cassette 26 may be removed from the device 20 by releasing latching members 202 and 204. The removed cassette, with its tray of tissue bearing stylets, can then be transported to the laboratory safely (shown by the phantom lines in FIG. 5) and without the danger of injury to personnel or to the tissue samples. Moreover, the cassette can be immersed in a fluid which prevent the samples from drying out prior to testing. If additional tissue samples are needed of the patient a new cassette can be inserted in the device while the device remains in place with the cannula extending into the patient's body.

The cassette, its tray and the stylets held therein, and the cannula assembly are preferably in the form of a replaceable, disposable kit arranged for use with the automatic biopsy device 20 described heretofore. Thus, no manual handling of the stylets is required, and they can be maintained in sterile condition.

As stated previously, the embodiment shown herein uses a pneumatic system, operated by compressed carbon dioxide, to drive the stylets and cannula forward and then in reverse. However, the invention will work just as well with other gases or with other types of powered drives, such as hydraulic or electric. Furthermore, although the embodiment disclosed herein shows a cassette tray with six stylets for the taking of six biopsies, cassettes with more or less stylets can be provided. Moreover, the length of the stylets may be selected to control the depth of penetration provided thereby. Thus, for some applications shorter stylets may be used and for other applications longer stylets may be used.

As should be appreciated from the foregoing, an automatic biopsy device of this invention enables a surgeon, using one hand, to take a plurality of biopsies in rapid sequence by successively depressing a trigger. The device may be powered by electric, pneumatic, hydraulic or other means. At the conclusion of the taking of the biopsies, the cassette with the stylets 34A-34F having tissue samples 200 therein can be removed by merely releasing the latches 202 and 204. The cassette can then be taken to the laboratory for study and analysis, with the cassette's body protecting the samples and the personnel handling the samples.

Moreover, the device 20 of this invention does not require the manual piercing of the tissue to take the specimen and assures that the biopsy is taken at the proper location, because the length of the stylets determine the penetration into the body and into the organ to be sampled. This is particularly advantageous because existing devices do not protect against under-insertion of the stylet, which results in a sampling of the wrong tissues, or over-insertion of the stylets which can cause damage to the organ.

Without further elaboration the foregoing will so fully illustrate our invention that others may by applying current or future knowledge, readily adapt the same for use under the various conditions of service.

We claim:

1. A device for taking a plurality of samples of tissue from a living being, comprising: a housing having a portion arranged to be held by a person using said device, a cannula having a proximal portion and a distal portion, said cannula being coupled to said housing adjacent said proximal portion of said cannula, a plurality of stylets located in said housing, each of said stylets having a proximal end, a distal end, and a recess located adjacent said distal end, and actuating means for selectively propelling each of said stylets through said cannula and into the body of said being so that a portion of said tissue enters into the recess of said selected stylet, said actuating means further propelling said cannula over said selected stylet to cause said distal portion to excise the portion of tissue within the recess of said selected stylet, said actuating means also being arranged to move said selected stylet and said cannula out of said tissue in the body of said being.

2. The device of claim 1 wherein each of said stylets is brought back into said housing by said actuating means after it has been moved out of said tissue.

3. The device of claim 2 additionally comprising a cassette in which said stylets are located, and wherein each of said stylets is brought back into said cassette by said actuating means after it has been moved out of said tissue.

4. The device of claim 3 wherein said actuating means propels said stylets and said cannula very quickly to minimize pain to said being.

5. The device of claim 3 additionally comprising a tray located within said cassette for holding said stylets thereon.

6. The device of claim 5 wherein said tray is moveable within said cassette under control of said actuating means to bring a selected stylet into axial alignment with said cannula.

7. The device of claim 5 wherein said tray comprises a plurality of grooves and each of said plurality of stylets is positioned in a respective one of said grooves.

8. The device of claim 7 additionally comprising positioning means for moving said tray, said positioning means comprising a plurality of detents, each one of said detents associated with a respective one of said grooves, said positioning means further comprising spring biased member for selectively engaging said detents.

9. The device of claim 3 additionally comprising latching means for releasably securing said cassette to said device.

10. The device of claim 2 wherein said actuating means propels said stylets and said cannula very quickly to minimize pain to said being.

11. The device of claim 1 additionally comprising a cassette in which said stylets are located.

12. The device of claim 11 wherein said actuating means propels said stylets and said cannula very quickly to minimize pain to said being.

13. The device of claim 11 additionally comprising a tray located within said cassette for holding said stylets thereon.

14. The device of claim 13 wherein said tray is moveable within said cassette under control of said actuating means to bring a selected stylet into axial alignment with said cannula.

15. The device of claim 14 wherein said cassette with said tray holding said stylets therein is releasably securable to said housing.

16. The device of claim 15 wherein said cannula is releasably secured to said device.

17. The device of claim 13 wherein said cassette with said tray holding said stylets therein is releasably securable to said housing.

18. The device of claim 13 wherein said tray comprises a plurality of grooves and each of said plurality of stylets is positioned in a respective one of said grooves.

19. The device of claim 11 wherein said cannula is releasably secured to said device.

20. The device of claim 11 wherein said cassette comprises a base and a cover.

21. The device of claim 1 wherein said actuating means propel said stylets and said cannula very quickly to minimize pain to said being.

22. The device of claim 1 wherein said actuating means comprises triggering means located on said portion of said housing.

23. The device of claim 22 wherein said actuating means operates pneumatically operative in response to said triggering means.

24. The device of claim 23 wherein said actuating means comprises a first pneumatic cylinder being arranged to be coupled to said stylets and a second pneumatic cylinder coupled to said cannula.

25. The device of claim 24 wherein said actuating means additionally comprises a first reversing valve coupled to said first pneumatic cylinder and a second reversing valve coupled to said second pneumatic cylinder.

26. The device of claim 24 wherein said propulsion of said cannula over said selected stylet occurs in automatic response to the propulsion of said stylet to a predetermined position within said cannula.

27. The device of claim 22 wherein said actuating means comprises a first pneumatic cylinder being arranged to be selectively coupled to said stylets and a second pneumatic cylinder coupled to said cannula.

28. The device of claim 27 wherein said actuating means additionally comprises a first reversing valve coupled to said first pneumatic cylinder and a second reversing valve coupled to said second pneumatic cylinder.

29. The device of claim 27 wherein said propulsion of said cannula over said selected stylet occurs in automatic response to the propulsion of said stylet to a predetermined position within said cannula.

30. The device of claim 29 additionally comprising switch means activated by the movement of said selected stylet to a predetermined position with respect to said cannula to cause said second pneumatic cylinder to operate to propel said cannula over said selected stylet.

31. The device of claim 1 wherein said actuating means operates pneumatically.

32. The device of claim 1 wherein said propulsion of said cannula over said selected stylet occurs in automatic response to the propulsion of said stylet to a predetermined position within said cannula.

33. The device of claim 32 additionally comprising switch means activated by the movement of said selected stylet to a predetermined position with respect to said cannula to cause said actuating means to operate to propel said cannula over said selected stylet.

34. The device of claim 1 additionally comprising a tray located within said housing for holding said stylets thereon.

35. The device of claim 34 wherein said tray is moveable within said housing under control of said actuating means to bring a selected stylet into axial alignment with said cannula.

36. The device of claim 1 wherein said cannula is releasably secured to said device.

* * * * *